United States Patent [19]

Meyer-Bisch

[11] Patent Number: 5,239,872
[45] Date of Patent: Aug. 31, 1993

[54] APPARATUS FOR THE PURPOSE OF MEASURING THE SENSITIVITY OF A SUBJECT TO THE PERCEPTION OF A VIBRATION

[76] Inventor: Christian Meyer-Bisch, 82 rue Stanislas, F-54000 Nancy, France

[21] Appl. No.: 965,620

[22] Filed: Oct. 22, 1992

Related U.S. Application Data

[63] Continuation of Ser. No. 655,425, Feb. 21, 1991, filed as PCT/FR90/00450, Jun. 20, 1990, abandoned.

[30] Foreign Application Priority Data

Jun. 23, 1989 [FR] France ............... 89/08397

[51] Int. Cl.⁵ ................... A61B 1/22; A61B 5/12
[52] U.S. Cl. .................... 73/585; 128/746
[58] Field of Search ................. 73/585; 128/746

[56] References Cited

U.S. PATENT DOCUMENTS

| | | | |
|---|---|---|---|
| 3,809,811 | 5/1974 | Delisle et al. | 73/585 |
| 4,038,496 | 7/1977 | Feezor | 73/585 |
| 4,615,007 | 9/1986 | King et al. | 364/42 |

FOREIGN PATENT DOCUMENTS 2033641  5/1980  United Kingdom .

OTHER PUBLICATIONS

H. Ide et al, "Relation Between Vibratory Sensibility and Electric Signal of Living Body", *Medical and Biological Engineering*, Sep. 1973, pp. 603–608.

Primary Examiner—Hezron E. Williams
Assistant Examiner—Rose M. Finley
Attorney, Agent, or Firm—Hill, Steadman & Simpson

[57] ABSTRACT

An apparatus for measuring the sensitivity of the subject to a perception of a vibration comprises a vibration emitter, a signal device which can be activated by the subject as a perception threshold is cross, and an electronic processing unit which includes devices for storing the frequency and level of vibration of each crossing, a device for controlling the frequency and level of vibration, a device for exploring a reference frequency level by a frequency scan and a device for searching the perception threshold corresponding to the vibration levels different from the reference level, by a series of iterative frequency scans carried out starting from a zone of non-perception and ending towards either a high frequency or a low frequency as soon as the perception threshold is reached.

17 Claims, 2 Drawing Sheets

APPARATUS FOR THE PURPOSE OF MEASURING THE SENSITIVITY OF A SUBJECT TO THE PERCEPTION OF A VIBRATION

This is a continuation of application Ser. No. 07/655,425, filed Feb. 21, 1991 now abandoned.

The invention relates to an apparatus for the purpose of measuring the sensitivity of a subject to the perception of a vibration.

If the vibration generates a sound, such an apparatus can be used for measuring the auditory acuity of a subject and it then acts as an audiometer. The most widespread audiometers are those for the purpose of tonal audiometry by conduction through the air, which consists in applying pure sounds at variable levels of acoustic pressure by means of ear-phones so as to determine the threshold of auditory perception of the subject at different frequencies.

As an audiometer, the apparatus of the invention can also be used to obtain audiometric measurements by bone conduction.

It can also be used to obtain measurements of the threshold of peripheral sensitivity.

The manual audiometric method is still to date the most used. It employs a sound generator which emits, for a series of specified frequencies, sounds at variable levels. For example, by activating a press-button, the subject signals to the investigator when the hearing threshold is crossed. In this way it is possible to plot the corresponding audiogram. The accuracy of this audiogram depends on the number of frequencies used (in general seven or nine), on the step size of the level, on the cooperation of the subject being tested, on the level of background noise, on the investigator who must be well trained, and finally on the time required to carry out this test.

In order to limit the subjective aspects of the manual method, different automatic devices have been devised.

One of these emits in succession sounds at fixed frequencies. For each of the frequencies, the sound level increases progressively. As soon as the subject indicates that he hears the sound, that is to say that his threshold for auditory perception has been exceeded, the level of sound reduces until he indicates that he no longer hears it. After a period, the same process is repeated for another frequency.

For each frequency, the excursions are recorded, and presented as a graph which is subsequently interpreted.

This technique can give good results when the subject is particularly skillful and is paying attention, but experience shows that the excursions obtained are often of large amplitude and make the audiograms very difficult to interpret.

Audiometers require a calibration step. In some of them level/frequency pairs are controlled with the help of a microprocessor in such a way that the response of the apparatus during a frequency scan supplies a flat response (U.S. Pat. No. 4,615,007).

In another kind of automatic apparatus employing the method called the "Bekezy method", sounds are emitted at increasing and decreasing levels as a function of the response of the subject being tested. But here, at the same time as the variation of the sound level, the apparatus causes the frequency to shift so as to explore a wide spectrum (for example from 125 to 8000 Hz). The document U.S. Pat. No. 4,038,496 describes a portable audiometer allowing this method to be employed.

This method which has a number of advantages also has a certain number of disadvantages which have restricted its general use. In fact, as the perception threshold is exceeded, a supraliminal sound is applied, which induces a saturation phenomenon comparable to dazzling which impairs the accuracy of the next measurements. Moreover, the fact that the frequency scan continues even though the subject does not hear and that the level increases, leads to an uncertainty in measurement which can be significant.

The aim of the present invention is to provide an apparatus for the purpose of measuring the perception sensitivity of a subject to a vibration, which allows automatic measurements to be carried out with good accuracy and which avoids the disadvantages of previously known apparatuses.

For this purpose, the invention relates to an apparatus comprising a vibration emitter or emitter means for providing vibrations at a frequency and a level, means for signalling which can be activated by the subject as the perception threshold is crossed, an electronic processing unit storing the frequency and the level of the vibration each time the perception threshold of the subject is crossed and controlling the frequency and level of the emitted vibration.

According to the invention, the processing unit explores first of all a vibration reference level by a frequency scan, it then searches for the perception thresholds corresponding to vibration levels different from the reference level, by a series of iterative frequency scans, carried out starting from the zone of non-perception and ending towards the high frequencies and towards the low frequencies as soon as the perception threshold is reached.

The invention will be described in detail by reference to the attached drawings in which.

Figure 1:
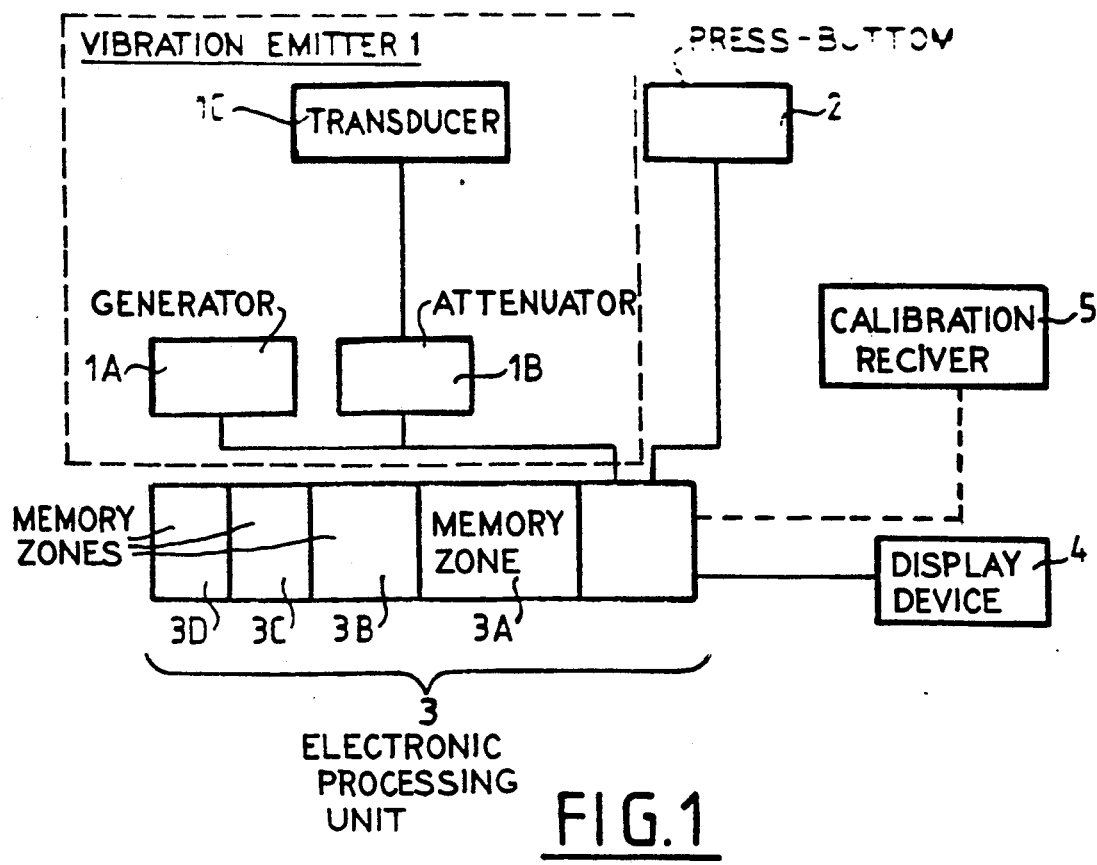
FIG. 1 is a schematic representation of the components of the apparatus of the invention.
Figure 2:
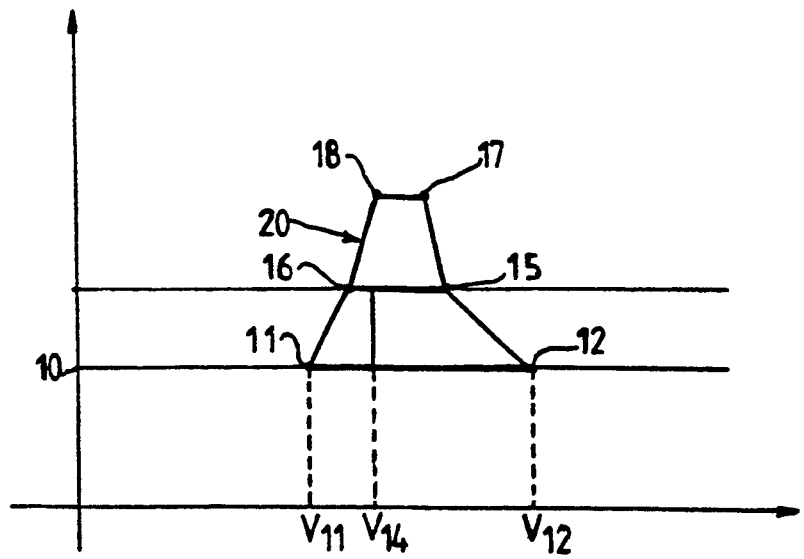
FIG. 2 is a representation on a level-frequency plot of the perception thresholds of a subject showing a zone of non-sensitivity.
Figure 3:
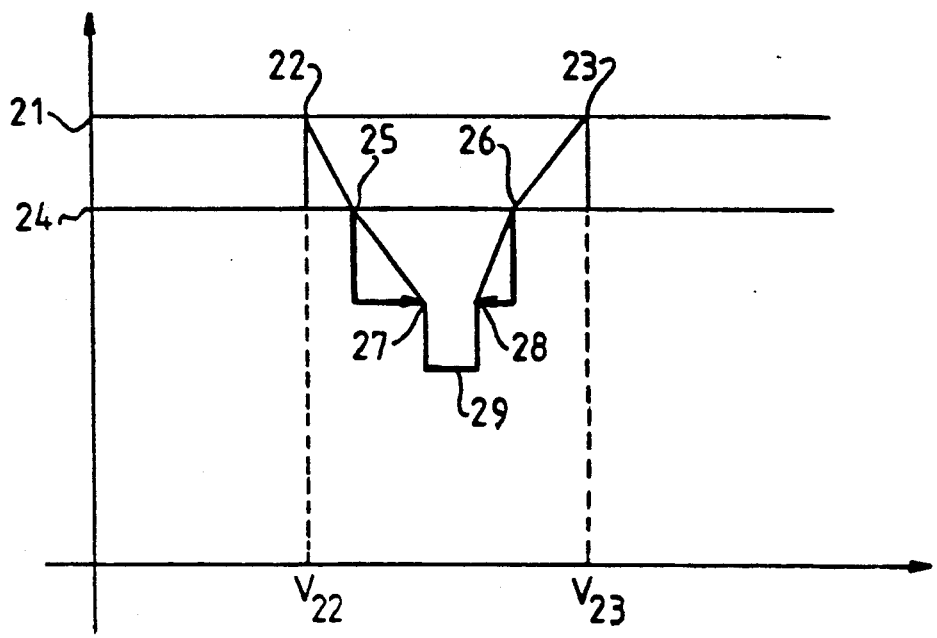
FIG. 3 is a representation on a level-frequency plot of the perception thresholds of a subject showing a zone of resonance.

The description which follows relates more especially to an audiometer. This is the preferred area of application of the invention. However, the invention can have many other applications, in particular it also relates to the measurement of peripheral sensitivity thresholds of a subject to vibrations, which is not yet a very widespread test, but does allow better understanding of the mechanisms involved, characterisation of certain disorders and contributions to formulating their correction.

The apparatus of the invention is particularly well suited to preventive screening, gives reproducible results, independent of the investigator, and allows tests to be carried out quickly.

This apparatus comprises a vibration emitter 1, which includes a sound generator 1A, an attenuator 1B and a transducer 1C, and a press-button 2 used by the subject as a means of signalling allowing him to indicate that his perception threshold has been exceeded. The vibration emitter is preferably an auditory headset such as defined in the standard 350 389 175.

It comprises an electronic processing unit 3. This involves a microcontroller for example of the type marketed under the designation "Motorola 68 HC 11"

which comprises a first memory zone 3A storing the frequency and the level of the vibration each time the hearing threshold of the subject is crossed. The processing unit 3 also comprises a second memory 3B for the purpose of receiving reference values of the vibration threshold corresponding for example to a "normal" population. By this means, it is possible to compare hearing thresholds of a subject with the reference values. The processing unit 3 also comprises a memory zone 3C containing the information from the various programs enabling the apparatus to function according to preset cycles. A memory zone 3D of the processing unit 3 contains calibration values.

The generator 1A is a hybrid generator capable of generating sounds whose frequency is variable from 125 to 16000 Hz. It comprises a microprocessor which transmits a 12 bit code to an analog-digital converter. This analog-digital converter controls a voltage-frequency converter which generates a sinusoidal signal. Preferably, the frequency of the signal is controlled in a manner to correct for possible drifts.

The attenuator 1B receives from the processing unit 3 an attenuation value worked out from a calibration curve and from the nominal attenuation value.

The processing unit 3 also controls the frequency and the level of the vibration emitted by the emitter 1. The generator 1A and the attenuator 1B determine respectively the frequency and the level of sound emitted by the transducer 1C. The processing unit 3 is connected to a display device 4 allowing the presentation of the audiogram, that is to say of the sound level as a function of the frequency corresponding to the hearing threshold of the subject. This display device can be a screen, a printer or a plotter. In a preferred embodiment, the apparatus comprises a liquid crystal screen of 240 dots per line and 128 lines which allows both the monitoring of the overall functioning of the apparatus as well as the displaying, in real time, of the audiogram of the subject. It also comprises a (silent) graphic thermal printer for example with 320 dots per line.

Perception threshold here means the pair of values of frequency-level parameters of the vibration corresponding for a specified frequency to the minimum level for which the subject perceives the vibration.

At the start of the measurement, the apparatus explore the base-line reference level 10 by a frequency scan.

In the case where the subject, by means of the push-button 2, indicates that he perceives the signal over the whole of the spectrum, the processing unit 3 can terminate the measurement. In the case of preventive screening, it can hence be concluded that the subject is healthy. The processing unit can also continue the measurement by reducing progressively the reference level until perception thresholds are detected.

By contrast, if the subject shows no sensitivity to the vibration in the course of this frequency scan, the processing unit explores higher vibration levels by the emission of sounds at several set frequencies until a response from the subject is obtained that then fixes the reference level.

The choice of the base-line reference level 10 and the possible successive modifications of this reference level are programmed as a function of the type of measurement that it is wished to carry out.

When the processing unit receives the signals emitted by the subject as the perception thresholds are crossed, it stores them and implements a series of iterative frequency scans carried out for each level starting from the zone of non-perception and finishing towards the high frequencies as well as towards the low frequencies as soon as the perception threshold is reached.

In this way, following the detection of two perception thresholds 11 and 12 at the reference level 10, separated by a zone of non-sensitivity, the processing unit controls the emission of new vibrations at a level 13 greater than the level 10 starting at the frequency V14 intermediate between the frequencies V12 and V11, that is to say situated in the zone of non-sensitivity of the subject. This scan towards the high frequencies allows the detection of the perception threshold 15 and towards the low frequencies the perception threshold 16.

In an iterative manner, the process carried out from perception thresholds 11 and 12 is reproduced from perception thresholds 15 and 16 allowing the detection o perception thresholds 17, 18 etc.

The pairs of vibration level-frequency values corresponding to the successively detected perception thresholds 11, 12, 15, 16, 17, 18 etc. are stored and used to plot the curve of perception sensitivity 20.

In this way, the apparatus has carried out an exploration of the "hole" corresponding to the zone of non-perception by examining in turn each of its boundaries. The distance between the various reference levels defines the accuracy of the measurement finally achieved.

When the subject has several zones of non-perception, each of the them will be examined in succession.

One of the important advantages of the apparatus of the invention which allows a measurement of good quality to be obtained is that by exploring the sensitivity of the subject from the zone of non-perception, it avoids all the faults likely to arise by saturation of the subject's sensitivity. At the same time, it has the advantages resulting from the frequency scans. It allows rapid measurements to be carried out, either by a single sweep allowing recognition of healthy subjects (screening), or by an exploration of only the zones carrying information.

Up until now the exploration of zones of non-perception have been described. There are subjects who, by contrast, react in an excessive and sometimes painful manner to vibrations of certain frequencies. In analogous fashion, these zones of "hypersensitivity" can be explored. The reference level instead of being progressively increased is then progressively reduced.

Here also, the apparatus of the invention allows the avoidance of sensitivity saturations, for example of hearing, the processing unit explores therefore the zones of hypersensitivity by stopping emission of the vibrations, when such a zone is reached.

When by scanning at a reference level 21 a zone of resonance between two perception thresholds 22 and 23 is detected, a new scan is carried out by an emission at a lower level 24. The scan is carried out towards the high frequencies starting at the frequency V22 (within 5% for example) of the perception threshold 22 (level 21—low frequency) and is stopped as soon as the perception threshold 25 of the level 24 is reached. The scan towards low frequencies is carried out starting from the frequency V23 (within 5% for example) of the perception threshold 23 (level 24—high frequency) and is also stopped as soon as the perception threshold 26 of the level 24 is reached. In an iterative manner lower and lower levels are explored as perception thresholds are detected. The perception thresholds 22, 23, 25, 26, 27, 28, 29, etc. are stored in the zone 3A of the processing unit 3.

A calibration receiver 5 is used for the calibration of the emission sequence (processing unit 3—sound generator 1A—attenuator 1B—transducer 1C). In the case of audiometers, this calibration is standardised. The values of this calibration are retained in the memory zone 3D. Each audiometer, including its headset, supplies a particular calibration curve. When it is useful to be able to use the same apparatus with various headsets, various memory zones 3D, 3D', 3D" etc. can be provided, each of the zones retaining, for the same apparatus, the calibration curve corresponding to a particular headset. Before the measurement, the user supplies to the processing unit the necessary information relating to the headset used. The corresponding calibration curve is employed.

At the end of the exploration, the curve presenting the hearing thresholds on a level-frequency plot is displayed. Preferably, the reference curve is also displayed on the same plot, clearly emphasising the differences between the subject curve and the reference curve. The apparatus of the invention can be used to calculate various representative parameters from the audiogram, to ensure the management of this information while associating it with the identity of the subject, or to communicate with an external system for example through a standardised connection such as that termed "RS 332". The man/machine communication is then advantageously effected via a keyboard and a set of roll-down menus.

I claim:

1. In an apparatus for the purpose of measuring the sensitivity of a subject to a perception of a vibration, said apparatus comprising emitter means for providing a vibration at a frequency and at an intensity level; means for signalling, which can be activated by the subject as a perception threshold is crossed; and an electronic processing unit being connected to the means for signalling and the emitter means, said unit having means for storing the frequency and intensity level of the vibration of each crossing of the perception threshold of the subject and means for controlling the frequency and the intensity level of the vibrations being provided by the emitter means, the improvements comprising the processing unit having means for exploring a referenced vibration intensity level by a frequency scan, said unit having first means for creating a series of itinerant frequency scans carried out starting from a selected frequency and intensity level in a zone of non-perception, including a frequency scan toward a higher frequency until a perception threshold is reached and a separate frequency scan from the selected frequency toward a lower frequency until a perception threshold at a lower frequency is reached, and said unit having second means for searching for a perception frequency threshold, corresponding to each vibration intensity level different from a referenced intensity level by using the output of said first means.

2. In an apparatus according to claim 1, wherein the second means for searching exposes various equally spread out levels.

3. In an apparatus according to claim 1, wherein for a purpose of measuring a peripheral sensitivity of a subject, the emitter means is an electric vibrator.

4. In an apparatus according to claim 1, wherein for a purpose of measuring an auditory acuity of a subject, the emitter means is a sound emitter.

5. In an apparatus according to claim 1, which includes means displaying the perception thresholds stored by the electronic processing unit.

6. In an apparatus according to claim 5, wherein the means for displaying produces and displays a curve of the levels as a function of the frequency of the perception threshold.

7. In an apparatus according to claim 6, wherein the means for displaying displays reference values at the same time as the displaying of the curve.

8. In an apparatus according to claim 1, wherein the processing unit has means to limit the frequency scan between a lower frequency and a higher frequency which are chosen by the investigator.

9. In an apparatus according to claim 1, wherein said second means makes a search at a specified level starting from a frequency corresponding to a geometric means of the frequencies of the perception threshold of a previously explored lower level.

10. In an apparatus according to claim 9, wherein the second means for searching exposes various equally spread out levels.

11. In an apparatus according to claim 9, wherein for a purpose of measuring the peripheral sensitivity of a subject, the emitter means is an electric vibrator.

12. In an apparatus according to claim 1, wherein said second means makes a search for a specified level starting from frequencies of the perception threshold of a previously explored higher level.

13. In an apparatus according to claim 12, wherein the second means for searching exposes various equally spread out levels.

14. In an apparatus according to claim 12, wherein for a purpose of measuring the peripheral sensitivity of a subject, the emitter is an electric vibrator.

15. A method for measuring the sensitivity of a subject to a perception of a vibration utilizing an apparatus comprising an emitter means for providing a vibration at a frequency and at an intensity level, means for signalling, which can be activated by the subject as a perception threshold is crossed, and an electronic processing unit being connected to the means for signalling and emitter means, said unit having means for storing the frequency and intensity levels of vibrations of each crossing of the perception threshold of the subject, means for controlling the frequency and the intensity level of vibrations being provided by the emitter means, first means for creating a series of iterative frequency scans carried out from a starting frequency and an intensity level in a zone of non-perception and changing the frequency by selectively either increasing the frequency until a perception is reached or decreasing the frequency until a perception threshold is reached, said method comprising subjecting a subject to a vibration frequency scan at a referenced intensity level, determining the perception thresholds indicated by the subject, then continuing a second frequency scan at an intensity level different than the referenced level with the starting frequency being in a non-perception threshold is reached, and then returning to the starting frequency and scanning in the opposite direction until a perception threshold is reached, and recording the frequency and intensity level for each perception threshold indicated.

16. A method according to claim 15, wherein the starting frequency corresponds to a geometric means of the frequencies of a perception threshold of a previously explored lower level.

17. A method according to claim 15, wherein the second frequency scan is made of a specified intensity level lower than the previously explored level and at a starting frequency of a perception threshold of the previously explored level.

* * * * *